United States Patent [19]

Nagano et al.

[11] Patent Number: 5,728,894
[45] Date of Patent: Mar. 17, 1998

[54] METHOD FOR PRODUCING METHACROLEIN

[75] Inventors: Osamu Nagano; Toru Watanabe, both of Yokohama, Japan

[73] Assignee: Asahi Kasei Kogyo Kabushiki Kaisha, Osaka, Japan

[21] Appl. No.: 700,469

[22] PCT Filed: Jun. 21, 1995

[86] PCT No.: PCT/JP95/01234

§ 371 Date: Aug. 26, 1996

§ 102(e) Date: Aug. 26, 1996

[87] PCT Pub. No.: WO95/35273

PCT Pub. Date: Dec. 28, 1995

[30] Foreign Application Priority Data

Jun. 22, 1994 [JP] Japan .................... 6-140151

[51] Int. Cl.$^6$ .................................... C07C 45/34
[52] U.S. Cl. ................. 568/479; 502/305; 502/317; 502/314; 502/321
[58] Field of Search ............... 568/479; 502/305, 502/317, 314, 321

[56] References Cited

U.S. PATENT DOCUMENTS

| | | |
|---|---|---|
| 3,936,505 | 2/1976 | Oda et al. . |
| 4,025,565 | 5/1977 | Oda et al. . |
| 4,155,938 | 5/1979 | Yamamoto et al. . |
| 4,162,234 | 7/1979 | Grasselli et al. . |
| 4,186,152 | 1/1980 | Yamamoto et al. . |
| 4,537,874 | 8/1985 | Sato et al. . |
| 4,778,930 | 10/1988 | Grasselli et al. . |
| 5,138,100 | 8/1992 | Matsuura . |
| 5,276,178 | 1/1994 | Onodera et al. . |

FOREIGN PATENT DOCUMENTS

| | | |
|---|---|---|
| 0 077 675 A1 | 4/1983 | European Pat. Off. . |
| 0 102 641 | 3/1984 | European Pat. Off. . |
| 0 169 449 | 1/1986 | European Pat. Off. . |
| 0 267 5556 | 5/1988 | European Pat. Off. . |
| 0 279 374 | 8/1988 | European Pat. Off. . |
| 0 420 048 | 4/1991 | European Pat. Off. . |
| 0 460 932 | 12/1991 | European Pat. Off. . |
| 0 523 727 | 1/1993 | European Pat. Off. . |
| 2 279 465 | 2/1976 | France . |
| 2035517 | 3/1971 | Germany . |
| 43-13987 | 6/1968 | Japan . |
| 48-17253 | 5/1973 | Japan . |
| 52-111505 | 9/1977 | Japan . |
| 52-111506 | 9/1977 | Japan . |
| 55-44730 | 11/1980 | Japan . |
| 60-28824 | 2/1985 | Japan . |
| 60-161932 | 8/1985 | Japan . |
| 60-163830 | 8/1985 | Japan . |
| 62-36740 | 8/1987 | Japan . |
| 63-107745 | 5/1988 | Japan . |
| 63-122641 | 5/1988 | Japan . |
| 63-122642 | 5/1988 | Japan . |
| 63-315147 | 12/1988 | Japan . |
| 2-32017 | 7/1990 | Japan . |
| 2-227140 | 9/1990 | Japan . |
| 3-176440 | 7/1991 | Japan . |
| 3-109943 | 9/1991 | Japan . |
| 5-23596 | 2/1993 | Japan . |
| 1 523 772 | 9/1978 | United Kingdom . |

*Primary Examiner*—Gary Geist
*Assistant Examiner*—Sreeni Padmanabhan
*Attorney, Agent, or Firm*—Pennie & Edmonds LLP

[57] ABSTRACT

Disclosed is a method for producing methacrolein, which comprises subjecting isobutylene and/or tert-butanol to gas phase catalytic oxidation with a molecular oxygen-containing gas in the presence of an oxide catalyst composition represented by the formula $Mo_{12}Bi_aCe_bK_cA_dB_fO_g$, wherein A is Co solely, or a mixture of Co and Mg wherein the atomic ratio of Mg to Co is not more than 0.7, B is Rb, Cs or a mixture thereof, and a, b, c, d, e, f and g are, respectively, the specific atomic ratios of Bi, Ce, K, Fe, A, B and O, relative to 12 atoms of Mo. By the method of the present invention, it is possible to stably produce methacrolein in high yield, using an oxide catalyst composition which has a relatively simple structural composition and therefore can be easily prepared, and which has not only a prolonged catalyst life due to excellent thermal stability and reduction resistance, but also excellent selectivity for methacrolein, wherein the catalyst composition contains Bi, Ce, K and Fe in specific amounts and in a specific relative amount ratio, and does not contain such elements as cause environmental pollution and toxicity problems, and also does not require the use, as raw materials for the preparation thereof, compounds having low solubility in water, such as compounds of W, Sb and Nb, which exhibit desired catalytic performances but are disadvantageous because of difficulties in obtaining uniform catalyst compositions.

9 Claims, No Drawings

METHOD FOR PRODUCING METHACROLEIN

This is the U.S. National Stage Application of PCT/JP95/01234 filed Jun. 21, 1995 now WO/95/35273 published Dec. 28, 1995.

BACKGROUND OF THE INVENTION

1. Technical field

The present invention relates to a method for producing methacrolein. More particularly, the present invention is concerned with a method for producing methacrolein, which comprises subjecting at least one member selected from the group consisting of isobutylene and tert-butanol to gas phase catalytic oxidation with a molecular oxygen-containing gas in the presence of an oxide catalyst composition which has a specific, relatively simple structural composition and therefore can be easily prepared, and which has not only a prolonged catalyst life due to the excellent thermal stability and reduction resistance, but also excellent selectivity for methacrolein, wherein the catalyst composition contains bismuth, cerium, iron and potassium in specific amounts and in a specific relative amount ratio, and without such elements as have conventionally been necessarily used to achieve high catalytic performances despite the accompanying environmental pollution and toxicity problems, and also without the need for using, as raw materials for the preparation thereof, compounds having low solubility in water, such as a tungstate, an antimony compound and a niobium compound, which have frequently been used in order to achieve desired catalytic performances, but the use of which is disadvantageous because of difficulties in obtaining uniform catalyst compositions.

2. Prior art

Heretofore, various proposals have been made with respect to catalysts which can be used for production of methacrolein by gas phase catalytic oxidation of at least one member selected from the group consisting of isobutylene and tert-butanol. Most of such conventional techniques are directed to the choice of elements to be contained in the catalyst composition and atomic ratios of the elements. For example, there has been known a technique in which cerium is used as a component for a catalyst composition to thereby improve catalytic activities, especially, yield of methacrolein. However, the conventional catalysts proposed for producing methacrolein are still unsatisfactory with respect to other requirements for a catalyst than the yield of methacrolein, such as catalyst life, ease and safety in the preparation thereof, and freedom from the detrimental influence of the catalyst on the environment. Thus, there has been a strong demand for a catalyst for producing methacrolein, which is satisfactory in respect of the above-mentioned various requirements.

As examples of prior art patent documents, the working examples of which disclose the use of catalysts containing Ce, there can be mentioned German Patent No. 2035517 (corresponding to Examined Japanese Patent Application Publication No. 43-13987), Unexamined Japanese Patent Application Laid-Open Specification No. 60-161932, Unexamined Japanese Patent Application Laid-Open Specification No. 60-163830, Unexamined Japanese Patent Application Laid-Open Specification No. 63-107745, Unexamined Japanese Patent Application Laid-Open Specification No. 63-122641, European Patent No. 0 267 556 (corresponding to Unexamined Japanese Patent Application Laid-Open Specification No. 63-122642), Unexamined Japanese Patent Application Laid-Open Specification No. 2-227140, European Patent No. 0 420 048 (corresponding to Unexamined Japanese Patent Application Laid-Open Specification No. 3-109943), European Patent No. 0 523 727 (corresponding to Unexamined Japanese Patent Application Laid-Open Specification No. 5-23596), Unexamined Japanese Patent Application Laid-Open Specification No. 6-192144, Unexamined Japanese patent Application Laid-Open Specification No. 52-111505, European Patent No. 0 102 641 (corresponding to Examined Japanese Patent Application Publication No. 62-36740), U.S. Pat. No. 4,537,874 (corresponding to Examined Japanese patent Application publication No. 2-32017), European Patent No. 0 279 374 (corresponding to Unexamined Japanese Patent Application Laid-Open Specification No. 63-315147), U.S. Pat. No. 5,276,178 (corresponding to Unexamined Japanese Patent Application Laid-Open Specification No. 3-176440, Unexamined Japanese Patent Application Laid-Open Specification No. 3-200733, Unexamined Japanese Patent Application Laid-Open Specification No. 3-215441 and Unexamined Japanese patent Application Laid-Open Specification No. 3-294238), Examined Japanese Patent Application Publication No. 53-23808 (corresponding to U.S. Pat. Nos. 3,936,505 and 4,025,565) and Examined Japanese Patent Application Publication No. 55-44730. However, it is noted that the catalyst compositions used in the working examples of the above-mentioned patent documents necessarily contain, in addition to cerium, some of undesirable elements, such as thallium, tellurium, zinc, chromium, thorium, uranium, tungsten, antimony and niobium. The above-mentioned undesirable elements cause not only problems of toxicity and environmental pollution, but also difficulties in preparing a catalyst containing such elements or in recovery of such elements. Therefore, the techniques of the above-mentioned documents are unsatisfactory from the view-points of recent stringent requirements of prevention of environmental pollution, reduction of cost required for production of catalyst, ease in recycling elements contained in the catalyst. For example, compounds of tungsten, antimony and niobium have low solubility in water. Therefore, the use of these compounds for preparation of a catalyst composition is disadvantageous in that, due to the low solubility thereof in water, a large amount of water needs to be used for preparing slurry containing such compounds during the production thereof, or such compounds need to be pulverized prior to use. Specifically, when a large amount of water is used during the production of a catalyst composition, a large amount of energy is needed for drying the slurry containing the compounds and, even if the compounds have been pulverized prior to use, the catalyst composition obtained therefrom inevitably becomes non-uniform in respect of a catalytic activity thereof, thereby leading to a disadvantageously short catalyst life. Further, when the low concentration slurry of raw material compounds is spray-dried, quasispherical particles having a desired size cannot be obtained, so that a subsequent tableting operation cannot be conducted efficiently.

Further, even if a certain catalyst exhibits excellent catalytic performance, when the catalyst comprises too many different elements, the production process thereof inevitably becomes complicated. Further, in the case of the catalyst containing metallic elements which detrimentally influence the environment or form compounds having low solubility by the reaction of the metallic elements with acids or bases, not only the disposal of waste liquids formed during the production of the catalyst but also the recovery of the metallic elements from the used catalyst is needed.

Consequently, the total cost for the production of a catalyst containing such elements inevitably becomes high.

In Examined Japanese Patent Application Publication No. 55-45256, Unexamined Japanese Patent Application Laid-Open Specification No. 60-84243, Examined Japanese Patent Application Publication No. 59-45415 (each of these three references corresponds to U.S. Pat. Nos. 4,155,938 and 4,186,152), Unexamined Japanese Patent Application Laid-Open Specification No. 52-111506, U.S. Pat. No. 4,778,930 (corresponding to Unexamined Japanese Patent Application Laid-Open Specification No. 51-34107), British Patent No. 1523772 (corresponding to Examined Japanese Patent Application Publication No. 60-36812) and U.S. Pat. No. 4,162,234 (corresponding to Unexamined Japanese Patent Application Laid-Open Specification No. 61-18435), cerium-containing catalysts are disclosed, however, such catalysts also contain iron in an excessively large amount or contain nickel, so that the selectivity for methacrolein is not satisfactory.

On the other hand, a method for improving catalytic activities of a catalyst by using a rare earth element is disclosed in U.S. Pat. No. 5,138,100 (corresponding to Unexamined Japanese Patent Application Laid-Open Specification No. 4-41454). In the method of U.S. Pat. No. 5,138,100, two separately prepared types of specific compositions are mechanically mixed and calcined, thereby obtaining a catalyst. In this U.S. Patent, there is a description to the effect that the catalyst thus obtained has high catalytic activity and excellent selectivity for methacrolein. However, the technique of U.S. Pat. No. 5,138,100 is disadvantageous not only in that cumbersome operations are necessary for the separate preparation of two types of specific compositions, but also in that in a commercial scale production of the catalyst, the mechanical mixing of the compositions is likely to cause a non-uniformity in the composition of the resultant final catalyst. Such a non-uniformity in the mixed composition of the catalyst also causes a non-uniformity in catalytic activities, leading to a shortening of the catalyst life.

In the commercial scale practice of synthesis of methacrolein, there are serious problems in the following points. That is, the synthesis of methacrolein involves an oxidation reaction, which is accompanied by the generation of a large amount of heat. The generated heat is accumulated in the catalyst bed. The accumulated heat acts to lower the catalytic performances, and the catalyst is-caused to sustain a heat load, thereby causing the catalyst to deteriorate. In European Patent No. 0 102 641 (corresponding to Examined Japanese Patent Application Publication No. 62-36740), as a method for reducing a heat load sustained by a catalyst, it is proposed to use a catalyst in a ring form so as to alleviate the heat accumulation. In U.S. Pat. No. 5,276,178 (corresponding to Unexamined Japanese Patent Application Laid-Open Specification No. 3-176440 and Unexamined Japanese Patent Application Laid-Open Specification No. 3-200733), it is proposed that a catalyst bed is divided to provide a plurality of reaction zones and then, a plurality of catalysts having different activities are respectively charged in the plurality of reaction zones to obtain a non-uniform temperature distribution such as to prevent the occurrence of heat accumulation. In European Patent No. 0 460 932 (corresponding to Unexamined Japanese Patent Application Laid-Open Specification No. 4-41453), it is proposed to use silica in an amount of from 5 to 15 % by weight, based on the weight of catalyst, to improve the stability of the catalyst. However, the above techniques have various disadvantages. That is, the technique to use a catalyst in a ring form and the technique to divide a catalyst bed are, respectively, disadvantageous in that the physical strength of the catalyst is lowered and that the troublesome preparation of such a plurality of different catalysts must be conducted. On the other hand, the use of silica as a component of a catalyst lowers the selectivity for methacrolein. In the above context, from the viewpoint of prolonging catalyst life, it has been desired to improve the thermal stability of an oxide composition per se, which constitutes a catalyst.

In the above-mentioned oxidation reaction, an oxidation reaction and a reduction reaction are constantly, repeatedly occurring on the catalyst, and the catalyst can appropriately function as long as a good balance is maintained between the oxidation and reduction reactions. However, when the ratio of the amount of oxygen (contained in the molecular oxygen-containing gas) to the starting material is markedly lowered due, for example, to an erroneous operation or a local vigorous reaction, the catalyst is likely to be reduced, thereby causing a change in the crystallite phase of chemical species constituting the catalyst. As a result, the deterioration of the catalyst is unfavorably promoted. In European Patent No. 0 169 449 (corresponding to Unexamined Japanese Patent Application Laid-Open Specification No. 61-33234), it is proposed to oxidize a deteriorated catalyst to restore the catalytic activities. However, it has been desired to develop a catalyst inherently having an improved reduction resistance in order to achieve a prolonged catalyst life.

SUMMARY OF THE INVENTION

In the above situations, the present inventors have made intensive and extensive studies toward developing a catalyst composition which has a prolonged catalyst life due to excellent heat resistance and reduction resistance, as well as an excellent selectivity for methacrolein, and which has a structural composition as simple as possible and therefore can be easily prepared, wherein the catalyst composition has no necessity of using, as raw materials for the preparation thereof, compounds having low solubility in water (e.g., compounds of tungsten, antimony and niobium), and/or has no necessity of incorporating metallic elements of copper, zinc, manganese, chromium, cadmium, lead, arsenic, mercury, thallium, tellunium, selenium, thorium, uranium, fluorine, tungsten, antimony and niobium which are likely to cause environmental problems during the preparation of a catalyst and during the recovery of metallic elements from a used catalyst. That is, with respect to an oxide catalyst composition for use in a method-for producing methacrolein, which method comprises subjecting at least one member selected from the group consisting of isobutylene and tert-butanol with a molecular oxygen-containing gas to gas phase catalytic oxidation, the present inventors have selected molybdenum, bismuth, cerium, iron, cobalt, magnesium, potassium, rubidium and cesium as metallic elements for constituting an oxide catalyst composition, and have made intensive studies toward developing an oxide catalyst composition having such desired properties and performances as mentioned above. As a result, it has unexpectedly, surprisingly been found that by choosing not only respective atomic ratios of the above-mentioned selected elements constituting an oxide catalyst composition but also a relative amount ratio of bismuth, cerium, potassium and iron so as to satisfy specific requirements, a catalyst composition can be provided which exhibits excellent properties and performances such that it has not only a prolonged catalyst life due to excellent thermal stability and reduction resistance, but also excellent selectivity for methacrolein, without containing such elements as have conventionally been necessarily used to achieve high catalytic performances despite the accompanying environmental pollution and toxicity problems, and also without the need for using, as raw materials for the preparation thereof, compounds having low solubility in water, such as a tungstate, an antimony compound and a niobium compound, which have conventionally, frequently been used in order to achieve desired catalytic activities, but the use of which is disadvantageous because of difficulties in obtaining uniform catalyst compositions. The present invention has been made, based on these novel findings.

Accordingly, it is an object of the present invention to provide a method for producing methacrolein, which comprises subjecting at least one member selected from the group consisting of isobutylene and tert-butanol to gas phase catalytic oxidation with a molecular oxygen-containing gas in the presence of an oxide catalyst composition, the oxide catalyst composition being such that it has a specific, relatively simple structural composition and therefore can be easily prepared, and that it not only causes no environmental pollution, but also exhibits excellent properties and performances, which are desired in the commercial scale practice of production of methacrolein, such as an excellent heat resistance, an excellent reduction resistance, a prolonged catalyst life and an excellent yield of methacrolein.

The foregoing and other objects, features and advantages of the present invention will be apparent from the following detailed description and appended claims.

DETAILED DESCRIPTION OF THE INVENTION

According to the present invention, there is provided a method for producing methacrolein, which comprises subjecting at least one member selected from the group consisting of isobutylene and tert-butanol to gas phase catalytic oxidation with a molecular oxygen-containing gas in the presence of an oxide catalyst composition represented by the formula (I):

$$Mo_{12}Bi_aCe_bK_cFe_dA_eB_fO_g \qquad (I)$$

wherein:

A is cobalt solely, or a mixture of cobalt and magnesium wherein the atomic ratio of magnesium to cobalt is not more than 0.7, B is rubidium, cesium or a mixture thereof, and a, b, c, d, e, f and g are, respectively, the atomic ratios of bismuth, cerium, potassium, iron, A, B and oxygen, relative to twelve atoms of molybdenum, wherein $0<a\leq 8$, $0<b\leq 8$, $0<c\leq 1.2$, $0<d\leq 2.5$, $1.0\leq e\leq 12$, $0<f\leq 2.0$, and g is the number of oxygens required to satisfy the valence requirements of the other elements present; and wherein a, b, c and d satisfy the requirements of the following fomulae:

$0.05\leq b/(a+b+c)\leq 0.7$, $0<c/(a+b+c)\leq 0.4$, and $0<d/(a+b+d)\leq 0.9$.

In the present invention, bismuth (Bi) is an indispensable component of an oxide catalyst composition for synthesizing methacrolein. Further, for providing an oxide catalyst composition capable of exerting the catalytic performances aimed at in the present invention, it is necessary that the atomic ratio (a) of bismuth, relative to twelve atoms of molybdenum, satisfy the relationship $0<a\leq 8$.

In the present invention, cerium (Ce) is indispensable for imparting a heat resistance and a reduction resistance to the oxide catalyst composition. For providing an oxide catalyst composition capable of exerting the catalytic performances aimed at in the present invention, it is necessary that the atomic ratio (b) of cerium, relative to twelve atoms of molybdenum, satisfy the relationship $0<b\leq 8$.

In the present invention, potassium (K) is indispensable for not only further enhancing the effect of addition of cerium, but also for improving the selectivity for methacrolein. For attaining these purposes, it is necessary that the atomic ratio (c) of potassium, relative to twelve atoms of molybdenum, satisfy the relationship $0<c\leq 1.2$. When c is more than 1.2, it becomes impossible to obtain a catalyst composition having desired catalytic activity, even if not only the amounts of the other elements than potassium but also the calcination and firing temperatures are appropriately regulated.

In the present invention, iron (Fe) is indispensable, similarly to bismuth, for commercial scale synthesis of methacrolein. However, when too large an amount of iron is contained in the oxide catalyst composition, the amount of by-products, such as carbon monoxide and carbon dioxide, is likely to increase, thus lowering the selectivity for methacrolein. Therefore, it is necessary that the atomic ratio (d) of iron, relative to twelve atoms of molybdenum, satisfy the relationship $0<d\leq 2.5$.

Further, with respect to the iron component, the relative amount ratio of iron to bismuth and cerium is also important for providing a catalyst composition exerting excellent catalytic performances. Specifically, it is necessary that a, b and d in formula (I) satisfy the relationship $0<d/(a+b+d)\leq 0.9$, preferably $0.1\leq d/(a+b+d)\leq 0.5$. From the viewpoint of achieving high selectivity for methacrolein, it is particularly important that the iron component satisfy both of the relationships $0<d\leq 2.5$ and $0<d/(a+b+d)\leq 0.9$ simultaneously.

To enhance further the heat resistance and reduction resistance imparted by the addition of cerium, while maintaining the selectivity for methacrolein, it is necessary that the relative amount ratio of bismuth, cerium and potassium be within a specific range. Specifically, it is necessary that a, b and c in formula (I) satisfy the relationship $0.05\leq b/(a+b+c)\leq 0.7$, preferably $0.1\leq b/(a+b+c)\leq 0.5$.

With respect to the potassium component, which is an indispensable element for synergistically improving the effect of the addition of cerium, the relative amount ratio of potassium to bismuth and cerium is important. Specifically, it is necessary that a, b and c in formula (I) satisfy the relationship $0<c/(a+b+c)\leq 0.4$, preferably $0.02\leq c/(a+b+c)\leq 0.2$.

The reason why the excellent performances aimed at in the present invention can be exerted when the relative amount ratio of bismuth, cerium and potassium satisfies the above-mentioned requirements has not yet been elucidated. However, it is believed to be as follows. When bismuth, cerium and potassium are used in a specific relative amount ratio, molybdic acid compounds respectively of bismuth, cerium and potassium undergo solid solubilization, thus exerting advantageous performances desired in the present invention.

In the present invention, cobalt (Co), as A in formula (I), is indispensable for improving the catalytic activity of the oxide catalyst composition without lowering the selectivity for methacrolein. Specifically, it is necessary that the atomic ratio (e) of cobalt, relative to twelve atoms of molybdenum, satisfy the relationship $1.0 \leq e \leq 12$.

In A of formula (I), magnesium is an element which can be used in partial substitution for, but cannot be used in entire substitution for the cobalt component. The use solely of magnesium as A cannot satisfactorily improve the catalytic activities of the catalyst composition. However, with respect to the cost of a starting material, a magnesium material is less expensive than a cobalt material. Therefore, it is commercially advantageous to be able to use magnesium in partial substitution for the cobalt component from the view-point of reduction of cost. When a mixture of magnesium and cobalt is used as A in formula (I), it is necessary that the atomic ratio of magnesium to cobalt is 0.7 or less and that the atomic ratio (e) of A, relative to twelve atoms of molybdenum, satisfy the relationship $1.0 \leq e \leq 12$, as in the case of the use solely of cobalt as A.

In the present invention, for further improving the selectivity for methacrolein, it is necessary that rubidium, cesium or a mixture thereof, as B in formula (I), be used in the catalyst composition. Specifically, it is necessary that atomic ratio (f) of B, relative to twelve atoms of molybdenum, satisfy the relationship $0 < f \leq 2.0$, preferably $0.1 \leq f \leq 1.0$. When f is more than 2.0, it becomes impossible to obtain a catalyst composition having a satisfactory catalytic activity even if not only the amounts of the other elements than rubidium and cesium but also the calcination and firing temperatures are appropriately regulated.

On the other hand, nickel (which is in the same series in the Periodic Table as cobalt) is another element which can be used in partial substitution for the cobalt component in the present invention. However, the presence of nickel in a catalyst composition unfavorably promotes the generation of by-products, such as carbon oxide and carbon dioxide. Therefore, it is not preferred to use nickel in the catalyst composition. When the use of a certain starting material is needed for some reasons even if it contains nickel as an impurity, care must be taken so that the atomic ratio of nickel, relative to twelve atoms of molybdenum, should not exceed 1.

The oxide catalyst composition to be used in the present invention can be produced by a conventional method. For example, the oxide catalyst composition can be produced by a method, comprising the steps of (1) preparing a slurry of starting materials, (2) spray-drying the slurry prepared in step (1) above to obtain a dried particulate catalyst precursor, and step (3) subjecting the dried particulate catalyst precursor obtained in step (2) above to calcination and final firing.

Hereinbelow, explanation is made with respect to a preferred embodiment of the above-mentioned method for producing the oxide catalyst composition to be used in the present invention, which comprises the steps of (1), (2) and (3).

In step (1), a slurry of starting materials is prepared. In the starting materials, each of the elements (which are to be incorporated into a catalyst composition), i.e., molybdenum, bismuth, cerium, potassium, iron, cobalt, magnesium, rubidium and cesium, may be present in the form of an ammonium salt, a nitrate, a chloride, a sulfate and an organic acid salt, which are soluble in water or nitric acid. Especially, it is preferred that a molybdenum source be in the form of an ammonium salt, and that each of bismuth, cerium, potassium, iron, cobalt, magnesium, rubidium and cesium be used in the form of a nitrate.

For example, the slurry of starting materials can be prepared by mixing a solution obtained by dissolving an ammonium molybdate in hot water and a solution obtained by dissolving nitrates of the other elements in water or an aqueous solution of nitric acid.

In step (2) the slurry obtained in the step (1) above is subjected to spray drying, to thereby obtain a quasispherical particulate catalyst precursor. The spray drying of the slurry can be generally conducted by centrifugation, two-phase flow nozzle method or high pressure nozzle method to obtain a dried particulate catalyst precursor. In this instance, it is preferred to use air which has been heated by an electric heater, steam or the like, as a heat source for drying. In this case, it is preferred that the temperature at an entrance to the dryer of the spray dryer be from 150° to 400° C. By the use of the dried particulate catalyst precursor thus obtained, it becomes possible to obtain the oxide catalyst composition in the form of an extruded catalyst, or preferably in the form of a tableted catalyst which is preferred because of uniformity in shape and density thereof.

In step (3), the dried particulate catalyst precursor obtained in step (2) above is calcined and finally fired to thereby obtain a desired oxide catalyst composition. The dried particulate catalyst precursor is calcined at a temperature of from 180° to 400° C. for about 1 to 24 hours, and, if desired, molded into a tablet having an appropriate shape, followed by final firing at a temperature of from 350° to 600° C. for 1 to 24 hours. For calcination and final firing, a kiln, such as a rotary kiln, a tunnel kiln or a muffle kiln, can be used.

In the present invention, it is preferred that the oxide catalyst composition be porous and have a pore diameter distribution such that the sum of pore volumes of pores having a pore diameter of 1 μm or less is 95% or more, based on the total pore volume of the oxide catalyst composition. By virtue of such a specific pore diameter distribution, not only are physical strength properties imparted to the catalyst composition per se, but also the diffusion velocity of molecules in the catalyst is controlled, thus preventing reactions in the catalyst composition from excessively advancing even when the catalyst composition experiences an unexpected sudden rise of temperature.

From the viewpoint of improving the selectivity for methacrolein, it is desirable that no silica be used or, if used, the amount of silica in the catalyst composition be as small as possible. However, when it is desired to increase the surface area of the catalyst composition so as to improve the activity thereof, silica may be used in a limited amount. Examples of silica sources include silica sol, silica gel, a silicate, such as potassium silicate or sodium silicate. In the catalyst composition, it is preferred that the atomic ratio of silica, relative to twelve atoms of molybdenum, be 3 or less, more preferably 1 or less, most preferably 0.1 or less, in terms of silicon (Si).

In the method of the present invention, the gas phase catalytic oxidation can be carried out by introducing a feedstock gas (comprising 1 to 10 % by volume of isobutylene, tert-butanol or a mixture thereof and 99 to 90% by volume of a gaseous mixture of a molecular oxygen-containing gas and a diluent gas) to a fixed bed reactor having a fixed catalyst bed of a (preferably tableted) catalyst comprised of the above-mentioned oxide catalyst composition, at a temperature of from 250° to 450° C. under a pressure of from atmospheric pressure to 5 atm, and at a space velocity of from 400 to 4,000/hr [under normal temperature and pressure (NTP) conditions].

Examples of molecular oxygen-containing gases include pure oxygen gas, and an oxygen-containing gas, such as air.

Examples of diluent gases include nitrogen, carbon dioxide, steam and a mixture thereof.

In the present invention, it is preferred that the volume ratio of the molecular oxygen to the above-mentioned gaseous mixture of a molecular oxygen-containing gas and a diluent gas satisfy the requirements of the formula 0.04<molecular oxygen/(molecular oxygen-containing gas+ diluent gas)<0.3, and that the concentration of molecular oxygen in the feedstock gas be from 4 to 20 % by volume.

For preventing the occurrence of coking on the catalyst composition, it is necessary that steam be contained in the feedstock gas. However, from the viewpoint of suppressing the by-production of carboxylic acids, such as methacrylic acid and acetic acid, it is preferred that a concentration of steam in a diluent gas be reduced to a level as low as possible. It is preferred that the amount of steam in the feedstock gas be generally from more than 0 to 30 % by volume.

BEST MODE FOR CARRYING OUT THE INVENTION

Hereinbelow, the present invention will be described in more detail with reference to the following Examples and Comparative Examples, but they should not be construed as limiting the scope of the present invention.

The number of oxygens in the catalyst composition is determined depending on the valence requirements of the other elements present. Therefore, in Examples and Comparative Examples, the number of oxygens in the catalyst composition is omitted from the formula representing the catalyst composition.

In the following Examples and Comparative Examples, the conversion and selectivity used for evaluating the results of the reaction are defined as follows:

$$\text{Conversion (\%)} = \frac{\text{mole of isobutylene or tert-butanol reacted}}{\text{mole of isobutylene or tert-butanol charged}} \times 100$$

$$\text{Selectivity (\%)} = \frac{\text{mole of methacrolein or methacrylic acid formed}}{\text{mole of isobutylene or tert-butanol reacted}} \times 100$$

EXAMPLE 1

An oxide catalyst composition having a structure (in terms of atomic ratios of constituent metallic elements, relative to twelve atoms of molybdenum) represented by the formula:

$$Mo_{12}Bi_{1.6}Ce_{0.4}Fe_{1.0}Co_{8.0}Cs_{0.4}K_{0.2}$$

was prepared as follows.

Ammonium heptamolybdate in the amount of 364 g was dissolved in 1820 g of water having a temperature of about 50 °C, to thereby obtain a solution (solution A). 133 g of bismuth nitrate, 29.8 g of cerium nitrate, 69.4 g of iron nitrate, 13.4 g of cesium nitrate, 3.46 g of potassium nitrate and 400 g of cobalt nitrate were dissolved in 290 g of a 15 wt % aqueous nitric acid solution, to thereby obtain a solution (solution B). Solutions A and B were mixed, while stirring for about 2 hours, thereby obtaining a slurry. The obtained slurry was subjected to spray drying, to thereby obtain a dried, particulate catalyst composition precursor. The obtained dried, particulate catalyst composition precursor was calcined at 200° C. for 3 hours, to thereby obtain a calcined catalyst composition precursor in the form of a quasispherical particle. The obtained calcined catalyst composition precursor was molded into a columnar tablet having a diameter of 5 mm and a height of 4 mm, and the tablet was subjected to final firing at 460° C. for 3 hours, thereby obtaining a final tableted catalyst composition. With respect to the obtained final tableted catalyst composition, the pore diameter distribution was measured using an Auto-Pore-9200 (automatic porosimeter manufactured and sold by Shimadzu Corporation, Japan). As a result, it was found that the sum of respective pore volumes of pores having a pore diameter of from 0.01 to 1.0 µm was 97%, based on the total pore volume of the catalyst composition, and the sum of respective pore volumes of pores having a pore diameter of from more than 1.0 to 10 µm was 2 %, based on the total pore volume of the catalyst composition.

The catalyst composition exhibited excellent physical strength due to the reduced number of pores having a large diameter. When the catalyst composition was allowed to fall by gravity in a tube having a diameter of 2.54 cm and a length of 3 m, breaking of the catalyst composition did not occur.

In order to evaluate the initial performances of the catalyst composition, 4.0 g of the tableted catalyst composition was charged into a reaction tube, made of stainless steel (JIS SUS304), having a diameter of 10 mm and being provided with a jacket. A gaseous mixture of 6% by volume of isobutylene, 10.8% by volume of oxygen, 10.0% by volume of steam and 73.2% by volume of nitrogen was flowed to the reactor at a flow rate of 100 ml/min (NTP), while maintaining the internal temperature of the reactor at 350° C., to thereby conduct a methacrolein synthesizing reaction. The results of the reaction were evaluated, and it was found that the conversion of isobutylene was 97.3%, the selectivity for methacrolein was 87.1%, and the selectivity for methacrylic acid was 2.5%.

Subsequently, the reaction temperature was elevated to 400 ° C. and the flow rate of the above-mentioned gaseous mixture was changed to 150 ml/min (NTP), and a continuous operation was conducted for about 4000 hours. Subsequently, the reaction conditions were changed to the same conditions as in the reaction for the evaluation of initial performances of the catalyst composition (reaction temperature: 350° C.; flow rate of gaseous mixture: 100 ml/min), and the results of the reaction were evaluated (life test of catalyst composition). As a result, it was found that the conversion of isobutylene was 97.4%, the selectivity for methacrolein was 87.2%, and the selectivity for methacrylic acid was 2.4%. As apparent from the above results, a lowering of the activity of the catalyst composition did not occur. Any discoloration or shrinkage of the catalyst composition was not observed.

EXAMPLE 2

A tableted catalyst composition having the same structural composition as that of the oxide catalyst composition prepared in Example 1 was prepared in substantially the same manner as in Example 1. With respect to the obtained catalyst composition, the pore diameter distribution was measured in substantially the same manner as in Example 1. The evaluation of initial performances was conducted with respect to 4.0 g of the tableted catalyst composition, in substantially the same manner as in Example 1, and the same results as in Example 1 were obtained (the conversion of isobutylene: 97.3%; the selectivity for methacrolein: 87.1%; the selectivity for methacrylic acid: 2.5 %). As a stringent-condition test, a methacrolein synthesizing reaction was conducted under conditions such that the reaction temperature was elevated to 455° C., and a gaseous mixture of 6 % by volume of isobutylene, 10.8% by volume of oxygen, 10.0% by volume of steam and 73.2% by volume of nitrogen was flowed to the reactor at a flow rate of 180 ml/min (NTP) for 24 hours. Subsequently, the reaction conditions were changed to the same conditions as in the reaction for the evaluation of initial performances of the catalyst composition (reaction temperature: 350° C.; flow rake of gaseous mixture: 100 ml/min). The results of the reaction were substantially the same as in the reaction for the evaluation of initial performances of the catalyst composition. That is, the conversion of isobutylene was 97.2%, the selectivity for methacrolein was 87.2%, and the selectivity for methacrylic acid was 2.5%.

Comparative Example 1

A tableted catalyst composition was prepared in substantially the same manner as in Example 1 except that the use of cerium nitrate was omitted. The obtained catalyst composition had a structure (in terms of atomic ratios of constituent metallic elements, relative to twelve atoms of molybdenum) represented by the formula:

$$Mo_{12}Bi_{2.0}Fe_{1.0}Co_{8.0}Cs_{0.4}K_{0.2}$$

With respect to the obtained catalyst composition, the pore diameter distribution was measured in substantially the same manner as in Example 1. The evaluation of the initial performances of the obtained catalyst was conducted in substantially the same manner as in Example 1, except that the gaseous mixture was flowed to the reactor at a flow rate 60 ml/min (NTP). The results of the reaction were evaluated, and it was found that the conversion of isobutylene was 97.3%, the selectivity for methacrolein was 84.0%, and the selectivity for methacrylic acid was 2.7%.

Subsequently, the reaction temperature was elevated to 400° C. and the flow rate of the above-mentioned gaseous mixture was changed to 90 ml/min (NTP), and a continuous operation was conducted for about 4000 hours. Subsequently, the reaction conditions were changed to the same conditions as in the reaction for the evaluation of initial performances of the catalyst composition (reaction temperature: 350° C.; flow rate of gaseous mixture: 60 ml/min), and the results of the reaction were evaluated (life test of catalyst composition). As a result, the conversion of isobutylene was 94.6%, the selectivity for methacrolein was 84.0%, and the selectivity for methacrylic acid was 3.4%. As apparent from the above results, a lowering of the activity of the catalyst composition occurred. A discoloration and a slight shrinkage of the catalyst composition were observed.

Comparative Example 2

A tableted catalyst composition having the same structural composition as that of the oxide catalyst composition prepared in Comparative Example 1 (containing no cerium) was prepared in substantially the same manner as in Comparative Example 1. With respect to the obtained catalyst composition, the pore diameter distribution was measured in substantially the same manner as in Example 1. With respect to 6.7 g of the obtained catalyst composition, the evaluation of initial performances and the stringent-condition test were conducted in substantially the same manner as in Example 2. As a result, the activity of the catalyst composition was drastically lowered. The conversion of isobutylene was as low as 70% or less. Further, there were observed a discoloration which is a criterion of the deterioration of the catalyst caused by the reduction, and a shrinkage which is a criterion of deterioration of the catalyst caused by heat. Results are shown in Table 1.

From comparison of the results of Examples 1 and 2 with the results of Comparative Examples 1 and 2, it is apparent that by the use of cerium in the catalyst composition, the heat resistance and reduction resistance of the catalyst composition were markedly improved, and the life of the catalyst composition was prolonged.

EXAMPLES 3 to 18

In Examples 3 to 18, tableted catalyst compositions having respective structural compositions as shown in Table 1 were prepared in substantially the same manner as in Example 1, except that the sources of metallic elements and amounts thereof were selected so as to comply with the respective oxide catalyst compositions indicated in Table 1. With respect to each of the obtained catalyst compositions, the pore diameter distribution was measured in substantially the same manner as in Example 1, and the evaluation of the initial performances and the stringent-condition test were conducted in substantially the same manner as in Example 2, except that the amount of catalyst composition used and/or the flow rate of the gaseous mixture was regulated so that performances of each of the catalyst compositions can be evaluated under conditions such that each of the catalyst compositions exhibits approximately the same conversion of isobutylene. Further, in each of Examples 5 and 8, the life test of the catalyst composition was conducted in substantially the same manner as in Example 1, except that in Example 5, the continuous operation was conducted for 3,000 hours. Results are shown in Table 1.

Comparative Examples 3 to 10

In Comparative Examples 3 to 10, tableted catalyst compositions having respective structural compositions as shown in Table 1 were prepared in substantially the same manner as in Example 1, except that the sources of metallic elements and amounts thereof were selected so as to comply with the respective oxide catalyst compositions indicated in Table 1. With respect to each of the obtained catalyst compositions, the pore diameter distribution was measured in substantially the same manner as in Example 1, and the evaluation of the initial performances and the stringent-condition test were conducted in substantially the same manner as in Example 2. Further, in each of Comparative Examples 5 and 6, the life test of the catalyst composition was conducted in substantially the same manner as in Example 1, except that in Comparative Example 5, the continuous operation was conducted for 3,000 hours. Results are shown in Table 2

With respect to relative atomic ratios of Bi, Ce and K, the results, shown in Table 1, of Examples and Comparative Examples clearly show that when the relationship $0.05 \leq b/(a+b+c) \leq 0.7$ is satisfied, the obtained catalyst composition exhibits excellent heat resistance and reduction resistance, whereas, when the catalyst composition contains cerium in such a large amount as falls within the range represented the formula: $0.7 < b/(a+b+c)$, the selectivity for methacrolein is lowered. From comparison of the results of Example 5 with the results of Comparative Example 5, and from comparison of the results of Example 8 with the results of Comparative Example 6, it is apparent that the life of the catalyst composition is influenced by the presence of potassium in the catalyst composition. From comparison of the results of Examples 1 and 4 with the results of Comparative Example 7, it is apparent that rubidium or cesium must be used in a catalyst composition for improving the selectivity for methacrolein. Further, from the results of Comparative Examples 8 and 9, it is apparent that, when nickel is used in partial substitution for the cobalt component, the selectivity for methacrolein is lowered.

Comparative Example 11

A tableted catalyst composition having a structure (in terms of atomic ratios of constituent metallic elements, relative to twelve atoms of molybdenum) represented by the formula:

$$Mo_{12}Bi_{1.6}Ce_{0.4}Fe_{1.0}Co_{8.0}Cs_{0.4}K_{0.2}$$

was prepared as follows.

In 1,200 ml of water were dissolved 127.2 g of ammonium molybdate and subsequently 5.0 g of cesium nitrate and 1.3 g of potassium nitrate, while heating and stirring, to thereby obtain a solution (solution A). 149.8 g of cobalt nitrate and 26.0 g of ferric nitrate were dissolved in 150 ml of water, to thereby obtain a solution (solution B). 49.9 g of bismuth nitrate was dissolved in an aqueous nitric acid solution comprising 26 ml of 60% nitric acid and 260 ml of water, to thereby obtain a solution (solution C). Solutions B and C were, in this order, dropwise added to solution A while mixing, and the resultant slurry was subjected to spray-drying, to thereby obtain a dried catalyst composition precursor. The obtained dried catalyst composition precursor was calcined in substantially the same manner as in Example 1, to thereby obtain composition (I) having an atomic ratio Mo/Bi/Fe/Co/Cs/K of 11.2/1.6/1/8/0.4/0.2.

Ammonium molybdate in the amount of 28.6 g was dissolved in 300 ml of water, while heating and stirring, to thereby obtain a solution (solution D). 35.2 g of cerium nitrate was dissolved in an aqueous nitric acid solution comprising 10 ml of 60% nitric acid and 100 ml of water, to thereby obtain a solution (solution E). Solution E was dropwise added to solution D while mixing, and the resultant mixture was neutralized with aqueous ammonia and heated at 100° C. while stirring for 8 hours, to thereby obtain a precipitate. The obtained precipitate was washed well with water, followed by drying and calcination, to thereby obtain composition (II) having an atomic ratio Ce/Mo of 0.5/1.

Compositions (I) and (II) were mixed so that the composition of the resultant mixture has the atomic ratio Mo/Bi/Ce/Fe/Co/Cs/K of 12/1.6/0.4/1/8/0.4/0.2. Distilled water was added to the mixture of compositions (I) and (II), while heating and stirring for 16 hours, followed by drying at 120° C. for 12 hours, to thereby obtain a dried catalyst composition. Subsequently, the obtained dried catalyst composition was subjected to final firing at 540° C. for 4 hours, to thereby obtain a final catalyst composition. The obtained final catalyst composition was pulverized, and molded into a columnar tablet having a diameter of 5 mm and a height of 4 mm. Using the obtained tableted catalyst composition, a methacrolein synthesizing reaction was conducted in substantially the same manner as in Example 1. Results of the reaction were evaluated in substantially the same manner as in Example 1. Results are shown in Table 1.

In this Comparative Example 11, it had been expected that the catalyst composition prepared in this Comparative Example exerts excellent performances as described in U.S. Pat. No. 5,138,100 (corresponding to Unexamined Japanese Patent Application Laid-Open Specification No. 4-41454). However, it was found that the selectivity for methacrolein was low. That is, although the conversion of isobutylene was 97.1%, the selectivity for methacrolein was as low as 75.3%, and the selectivity for methacrylic acid was 4.1%.

The difference between the catalyst composition prepared in Comparative Example 11 and the catalyst compositions used in Examples of U.S. Pat. No. 5,138,100 (corresponding to Unexamined Japanese Patent Application Laid-Open Specification No. 4-41454) consists only in that the catalyst compositions used in Examples of U.S. Pat. No. 5,138,100 do not contain alkali metals and the atomic ratio of iron (Fe) in each catalyst composition is more than 2.5, relative to twelve atoms of molybdenum, but the catalyst composition prepared in this Comparative Example 11 contains potassium and cesium and the atomic ratio of iron in the catalyst composition is 2.5 or less.

EXAMPLES 19 to 24

In Examples 19 to 24, tableted catalyst compositions having respective structural compositions as shown in Table 2 were prepared in substantially the same manner as in Example 1, except that the sources of metallic elements and amounts thereof were selected so as to comply with the respective oxide catalyst compositions indicated in Table 2. With respect to each of the obtained catalyst compositions, the pore diameter distribution was measured in substantially the same manner as in Example 1. In each Example, using respective catalyst compositions, a methacrolein synthesizing reaction was conducted in substantially the same manner as in the reaction for the evaluation of initial performances of the catalyst composition in Example 1, except that a gaseous mixture of 6.4% by volume of tert-butanol, 11.5% by volume of oxygen, 4.3% by volume of steam and 77.8% by volume of nitrogen was used, to thereby measure the selectivity for methacrolein, the selectivity for methacrylic acid and the ratio of by-produced isobutylene to tert-butanol. Further, a methacrolein synthesizing reaction was conducted in substantially the same manner as in the reaction for the stringent-condition test in Example 2, and the amount ratio of by-produced isobutylene to tert-butanol charged was measured. Results are shown in Table 2.

Comparative Example 12

A tableted catalyst composition having a structural composition as shown in Table 2, which is the same structural composition as that of the oxide catalyst composition prepared in Comparative Example 1 (containing no cerium), was prepared in substantially the same manner as in Example 1. With respect to the obtained catalyst composition, the pore diameter distribution was measured in substantially the same manner as in Example 1. Using the obtained catalyst composition, a methacrolein synthesizing reaction was conducted in substantially the same manner as in the reaction for the evaluation of initial performances of the catalyst composition in Example 1, except that a gaseous mixture of 6.4% by volume of tert-butanol, 11.5% by volume of oxygen, 4.3% by volume of steam and 77.8% by volume of nitrogen was used, to thereby measure the selectivity for methacrolein, the selectivity for methacrylic acid and the ratio of by-produced isobutylene to tert-butanol charged. Further, a methacrolein synthesizing reaction was conducted in substantially the same manner as in the reaction for the stringent-condition test in Example 2, and the amount ratio of by-produced isobutylene to tert-butanol charged was measured. Results are shown in Table 2.

As apparent from Table 2, also when tert-butanol is used, instead of isobutylene, in the feedstock gaseous mixture, the catalytic activity of a catalyst composition containing no cerium was low.

TABLE 1

| | Catalyst composition | Temperature for final firing of catalyst composition (°C.) | Pore volume ratio (%)*1 | Pore volume ratio (%)*2 | Conversion of isobutylene (%) | Selectivity for methacrolein % | Selectivity for methacrylic acid (%) | Conversion of isobutylene after test under stringent conditions (%) | Conversion of isobutylene after life test (%) |
|---|---|---|---|---|---|---|---|---|---|
| Example 1 | $Mo_{12}Bi_{1.6}Ce_{0.4}Fe_{1.0}Co_{8.0}Cs_{0.4}K_{0.2}$ | 460 | 97 | 2 | 97.3 | 87.1 | 2.5 | — | 97.4*4 |
| Example 2 | $Mo_{12}Bi_{1.6}Ce_{0.4}Fe_{1.0}Co_{8.0}Cs_{0.4}K_{0.2}$ | 460 | 97 | 2 | 97.2 | 87.2 | 2.5 | 97.2 | — |
| Example 3 | $Mo_{12}Bi_{1.7}Ce_{0.3}Fe_{2.0}Co_{7.0}Cs_{0.4}K_{0.2}$ | 500 | 96 | 2 | 97.5 | 86.4 | 2.9 | 97.4 | — |
| Example 4 | $Mo_{12}Bi_{1.8}Ce_{0.2}Fe_{1.5}Co_{8.0}Cs_{0.4}K_{0.2}$ | 500 | 95 | 3 | 97.3 | 86.4 | 2.7 | 97.2 | — |
| Example 5 | $Mo_{12}Bi_{1.6}Ce_{0.4}Fe_{1.5}Co_{8.0}Cs_{0.3}Rb_{0.1}K_{0.2}$ | 460 | 96 | 2 | 97.1 | 87.0 | 2.6 | 97.1 | 97.1*3 |
| Example 6 | $Mo_{12}Bi_{1.2}Ce_{0.4}Fe_{1.5}Co_{9.0}Rb_{0.3}K_{0.3}$ | 500 | 96 | 2 | 97.3 | 86.8 | 2.8 | 97.3 | — |
| Example 7 | $Mo_{12}Bi_{1.6}Ce_{0.4}Fe_{1.5}Co_{8.0}Cs_{0.3}Rb_{0.1}K_{0.2}$ | 460 | 98 | 1 | 97.2 | 87.2 | 2.4 | 97.1 | 97.1*4 |
| Example 8 | $Mo_{12}Bi_{2.0}Ce_{1.0}Fe_{1.0}Co_{6.5}Cs_{0.5}K_{0.1}$ | 480 | 97 | 2 | 97.1 | 86.6 | 2.8 | 97.3 | — |
| Example 9 | $Mo_{12}Bi_{2.0}Ce_{1.0}Fe_{2.5}Co_{5.0}Cs_{0.4}K_{0.1}$ | 490 | 97 | 2 | 97.2 | 86.4 | 3.1 | 97.1 | — |
| Example 10 | $Mo_{12}Bi_{1.2}Ce_{1.0}Fe_{1.0}Co_{8.0}Cs_{0.5}K_{0.2}$ | 480 | 98 | 1 | 97.3 | 86.5 | 2.7 | 97.5 | — |
| Example 11 | $Mo_{12}Bi_{1.0}Ce_{1.0}Fe_{1.0}Co_{8.0}Cs_{0.4}K_{0.2}$ | 480 | 98 | 2 | 97.6 | 86.2 | 2.8 | 97.5 | — |
| Example 12 | $Mo_{12}Bi_{0.0}Ce_{1.4}Fe_{1.0}Co_{8.0}Cs_{0.4}K_{0.2}$ | 500 | 95 | 2 | 97.4 | 86.0 | 2.7 | 97.4 | — |
| Example 13 | $Mo_{12}Bi_{1.6}Ce_{0.4}Fe_{1.2}Co_{8.0}Cs_{0.3}Rb_{0.2}K_{0.2}$ | 465 | 96 | 2 | 97.4 | 86.8 | 2.9 | 97.1 | — |
| Example 14 | $Mo_{12}Bi_{1.6}Ce_{0.4}Fe_{0.2}Co_{9.0}Cs_{0.5}K_{0.5}$ | 430 | 98 | 1 | 97.1 | 86.1 | 2.9 | 97.1 | — |
| Example 15 | $Mo_{12}Bi_{1.4}Ce_{0.4}Fe_{0.5}Co_{9.0}Cs_{0.3}K_{0.04}$ | 435 | 97 | 1 | 97.2 | 86.2 | 2.8 | 97.2 | — |
| Example 16 | $Mo_{12}Bi_{1.6}Ce_{0.4}Fe_{1.2}Co_{5.0}Mg_{2.0}Cs_{0.3}K_{0.3}$ | 470 | 97 | 1 | 97.3 | 86.9 | 2.7 | 97.3 | — |
| Example 17 | $Mo_{12}Bi_{1.6}Ce_{0.4}Fe_{1.2}Co_{4.0}Mg_{4.0}Cs_{0.3}K_{0.2}$ | 470 | 96 | 2 | 97.2 | 86.8 | 2.8 | 97.2 | — |
| Example 18 | $Mo_{12}Bi_{0.3}Ce_{0.05}Fe_{2.5}Co_{7.6}Cs_{0.5}K_{0.15}$ | 480 | 96 | 2 | 97.3 | 86.0 | 3.0 | 97.2 | — |
| Comp. Ex. 1 | $Mo_{12}Bi_{2.0}$ $Fe_{1.0}Co_{8.0}Cs_{0.5}K_{0.2}$ | 460 | 96 | 4 | 97.3 | 84.0 | 2.7 | — | 94.6*4 |
| Comp. Ex. 2 | $Mo_{12}Bi_{2.0}$ $Fe_{1.0}Co_{8.0}Cs_{0.5}K_{0.2}$ | 460 | 96 | 4 | 97.2 | 84.1 | 2.3 | 69.8 | — |
| Comp. Ex. 3 | $Mo_{12}Bi_{2.0}Ce_{1.0}Fe_{1.0}Co_{8.0}Cs_{0.5}K_{0.2}$ | 460 | 95 | 3 | 97.3 | 85.4 | 2.5 | 72.8 | — |
| Comp. Ex. 4 | $Mo_{12}Bi_{0.4}Ce_{1.0}Fe_{1.5}Co_{8.0}Cs_{0.4}K_{0.2}$ | 500 | 96 | 2 | 97.3 | 84.9 | 2.9 | 97.1 | — |
| Comp. Ex. 5 | $Mo_{12}Bi_{1.6}Ce_{0.4}Fe_{1.5}Co_{8.0}Rb_{0.2}$ | 460 | 97 | 1 | 97.0 | 87.1 | 2.5 | 97.1 | 95.9*3 |
| Comp. Ex. 6 | $Mo_{12}Bi_{2.0}Ce_{1.0}Fe_{1.0}Co_{5.5}Cs_{0.5}$ | 480 | 97 | 1 | 97.0 | 86.5 | 2.9 | 97.1 | 95.3*4 |
| Comp. Ex. 7 | $Mo_{12}Bi_{1.6}Ce_{1.0}Fe_{1.0}Co_{8.0}K_{0.2}$ | 540 | 95 | 3 | 97.4 | 71.4 | 4.8 | 97.3 | — |
| Comp. Ex. 8 | $Mo_{12}Bi_{1.6}Ce_{0.4}Fe_{1.2}Co_{6.0}Ni_{2.0}Cs_{0.3}Rb_{0.2}K_{0.2}$ | 465 | 95 | 3 | 97.2 | 85.4 | 3.2 | 97.3 | — |
| Comp. Ex. 9 | $Mo_{12}Bi_{1.6}Ce_{0.4}Fe_{1.2}Co_{4.0}Ni_{4.0}Cs_{0.3}Rb_{0.2}K_{0.2}$ | 465 | 95 | 2 | 97.5 | 82.6 | 3.5 | 97.4 | — |
| Comp. Ex. 10 | $Mo_{12}Bi_{1.6}Ce_{0.4}Fe_{3.0}Co_{8.0}Cs_{0.4}K_{0.2}$ | 480 | 96 | 2 | 97.3 | 75.6 | 4.2 | 97.1 | — |
| Comp. Ex. 11 | $Mo_{12}Bi_{1.6}Ce_{0.4}Fe_{1.0}Co_{9.0}Cs_{0.4}K_{0.2}$ | 540 | — | — | 97.1 | 75.3 | 4.1 | 97.0 | — |

*1: (Sum of pore volumes of pores having a pore diameter of from 0.01 to 1.0 μm/total pore volume) × 100
*2: (Sum of pore volumes of pores having a pore diameter of from more than 1.0 μm to 10 μm/total pore volume) × 100
*3: Conversion after continuous operation for about 3,000 hours
*4: Conversion after continuous operation for about 4,000 hours

TABLE 2

| Catalyst composition | Temperature for final firing of catalyst composition (°C.) | Pore volume ratio (%)*1 | Pore volume ratio (%)*2 | Evaluation of results of initial-stage reaction (by-produced i-$C_4^-$) (%) | Selectivity for methacrolein (%) | Selectivity for methacrylic acid (%) | By-produced i-$C_4^-$ after test under stringent conditions (%) |
|---|---|---|---|---|---|---|---|
| Example 19 | $Mo_{12}Bi_{1.6}Ce_{0.4}Fe_{1.0}Co_{8.0}Cs_{0.4}K_{0.2}$ | 460 | 97 | 2 | 2.8 | 86.2 | 2.6 | 2.9 |
| Example 20 | $Mo_{12}Bi_{1.6}Ce_{0.4}Fe_{1.5}Co_{8.0}Rb_{0.5}K_{0.2}$ | 500 | 95 | 3 | 2.8 | 86.5 | 2.5 | 2.7 |
| Example 21 | $Mo_{12}Bi_{1.7}Ce_{0.3}Fe_{1.2}Co_{8.0}Cs_{0.4}K_{0.2}$ | 500 | 96 | 2 | 2.9 | 85.3 | 2.9 | 2.8 |
| Example 22 | $Mo_{12}Bi_{1.8}Ce_{0.2}Fe_{1.0}Co_{8.0}Cs_{0.4}Rb_{0.1}K_{0.2}$ | 500 | 95 | 3 | 2.7 | 85.2 | 2.7 | 2.8 |
| Example 23 | $Mo_{12}Bi_{2.0}Ce_{0.4}Fe_{1.0}Co_{7.0}Cs_{0.4}K_{0.2}$ | 460 | 97 | 1 | 2.9 | 86.1 | 2.5 | 2.7 |
| Example 24 | $Mo_{12}Bi_{1.6}Ce_{0.4}Fe_{1.5}Co_{6.0}Mg_{2.0}Cs_{0.3}K_{0.3}$ | 470 | 97 | 1 | 2.8 | 86.2 | 2.7 | 2.8 |
| Comp. Ex. 12 | $Mo_{12}Bi_{2.0}\ Fe_{1.0}Co_{8.0}Cs_{0.4}K_{0.2}$ | 460 | 97 | 2 | 3.0 | 83.3 | 2.5 | 18.2 |

*1: (Sum of pore volumes of pores having a pore diameter of from 0.01 to 1.0 μm/total pore volume) × 100
*1: (Sum of pore volumes of pores having a pore diameter of from more than 1.0 μm to 10 μm/total pore volume) × 100
i-$C_4^-$: (Amount of by-produced isobutylene/Amount of tert-butanol charged) × 100

Industrial Applicability

According to the present invention, in a method for producing methacrolein, which comprises subjecting at least one member selected from the group consisting of isobutylene and tert-butanol to gas phase catalytic oxidation with a molecular oxygen-containing gas in the presence of an oxide catalyst composition, use is made of an oxide catalyst which has a specific, relatively simple structural composition and therefore can be easily prepared, and which has not only a prolonged catalyst life due to the excellent thermal stability and reduction resistance, but also excellent selectivity for methacrolein, wherein the catalyst composition contains bismuth, cerium, iron and potassium in specific amounts and in a specific relative amount ratio, and without such elements as have conventionally been necessarily used to achieve high catalytic performances despite the accompanying environmental pollution and toxicity problems, and also without the need for using, as raw materials for the preparation thereof, compounds having low solubility in water, such as a tungstate, an antimony compound and a niobium compound, which have frequently been used in order to achieve desired catalytic performances, but the use of which is disadvantageous from the viewpoint of difficulties in obtaining uniform catalyst compositions. Therefore, the production of methacrolein in high yield can be advantageously performed.

We claim:

1. A method for producing methacrolein, which comprises subjecting at least one member selected from the group consisting of isobutylene and tert-butanol to gas phase catalytic oxidation with a molecular oxygen-containing gas in the presence of an oxide catalyst composition represented by the formula (I):

  (I)

$Mo_{12}Bi_aCe_bK_cFe_dA_eB_fO_g$ wherein:

A is cobalt solely, or a mixture of cobalt and magnesium wherein the atomic ratio of magnesium to cobalt is not more than 0.7, B is rubidium, cesium or a mixture thereof, and a, b, c, d, e, f and g are, respectively, the atomic ratios of bismuth, cerium, potassium, iron, A, B and oxygen, relative to twelve atoms of molybdenum, wherein $0 < a \leq 8$, $0 < b \leq 8$, $0 < c \leq 1.2$, $0 < d \leq 2.5$, $1.0 \leq e \leq 12$, $0 < f \leq 2.0$, and g is the number of oxygens required to satisfy the valence requirements of the other elements present; and wherein a, b, c and d satisfy the requirements of the following formulae:

$0.05 \leq b/(a+b+c) \leq 0.7$, $0 < c/(a+b+c) \leq 0.4$, and $0 < d/(a+b+d) \leq 0.9$.

2. The method according to claim 1, wherein said A is cobalt solely.

3. The method according to claim 1, wherein said oxide catalyst composition is porous and has a pore diameter distribution such that the sum of pore volumes of pores having a pore diameter of 1 μm or less is 95% or more, based on the total pore volume of said oxide catalyst composition.

4. The method according to claim 1, wherein a, b and c in formula (I) satisfy the requirements of the formula: $0.1 \leq b/(a+b+c) \leq 0.5$.

5. The method according to claim 1, wherein a, b and c in formula (I) satisfy the requirements of the formula: $0.02 \leq c/(a+b+c) \leq 0.2$.

6. The method according to claim 1, wherein a, b and d in formula (I) satisfy the requirements of the formula: $0.1 \leq d/(a+b+d) \leq 0.5$.

7. The method according to claim 1, wherein said oxide catalyst composition is free of tungsten, antimony and niobium.

8. The method according to claim 1, wherein said oxide catalyst composition is free of copper, zinc, manganese, chromium, cadmium, lead, arsenic, mercury, thallium, tellurium, selenium, thorium, uranium, fluorine, tungsten, antimony and niobium.

9. The method according to claim 1, wherein said oxide catalyst composition represented by the formula (I) above is solely used as the catalyst.

* * * * *